United States Patent [19]
Yui et al.

[11] Patent Number: 5,618,312
[45] Date of Patent: Apr. 8, 1997

[54] MEDICAL MATERIALS AND MANUFACTURING METHODS THEREOF

[75] Inventors: Tooru Yui, Fujisawa; Tokuzo Nakagawa, Kanagawa; Kazuo Kondoh, Tokorozawa, all of Japan

[73] Assignee: Bio-Engineering Laboratories, Ltd., Tokyo, Japan

[21] Appl. No.: 630,683

[22] Filed: Apr. 12, 1996

[30] Foreign Application Priority Data

Oct. 31, 1995 [JP] Japan .................... 7-305259

[51] Int. Cl.⁶ ............................. A61L 17/00
[52] U.S. Cl. ............................. 606/229
[58] Field of Search ............ 606/228–231; 623/1–2, 7–8, 11–12, 15–16, 866; 424/35–37, 160–161, 27; 128/DIG. 8

[56] References Cited

U.S. PATENT DOCUMENTS

| | | | |
|---|---|---|---|
| 3,674,901 | 7/1972 | Shepherd et al. | 606/231 |
| 3,849,185 | 11/1974 | Shepherd et al. | 606/231 |
| 4,034,750 | 7/1977 | Seiderman | 606/229 X |
| 4,233,360 | 11/1980 | Luck et al. | 606/229 |
| 4,280,954 | 7/1981 | Yannas et al. | 606/229 X |
| 4,378,017 | 3/1983 | Kosugi et al. | 606/229 X |
| 4,394,370 | 7/1983 | Jeffries | 606/229 |
| 5,217,495 | 6/1993 | Kaplan et al. | 606/230 X |

*Primary Examiner*—Michael Powell Buiz
*Assistant Examiner*—Nancy Connelly Mulcare
*Attorney, Agent, or Firm*—Oblon, Spivak, McClelland, Maier & Neustadt, P.C.

[57] ABSTRACT

Disclosed are a medical material and a production process thereof. The medical material has a membrane configuration and is produced by impregnating a membranous material with collagen or gelatin and then physically or chemically cross-linking protein molecules of the membranous material. The membranous material is essentially acellular compact layer of a biogenic connective tissue. The medical material may further be processed into other forms such as threads, braids, tubes and hoses and is useful in surgery. The medical material has a strength sufficient to be useful for surgically stitching wounds either manually or mechanically.

10 Claims, No Drawings

MEDICAL MATERIALS AND MANUFACTURING METHODS THEREOF

FIELD OF THE INVENTION

The present invention relates to an artificial material to be applied to living bodies in surgery. More specifically, the present invention relates to various medical materials in the categories of surgical prosthetic material, wound and burn dressing, skin graft for donor site of grafting and artificial organs and their manufacturing methods.

BACKGROUND OF THE ART

In fields that use the materials described above, various kinds of synthetic or natural macromolecular materials have been utilized in assorted configurations. Medical materials in which the raw materials are biogenic portions from equine, swine and bovine sources have also been used. All such medical materials made by conventional techniques comprise materials that are heterologous or foreign to the human body. Consequently, such medical materials manufactured by conventional techniques are unable to eliminate completely the undesirable effects such as immune reaction and reaction to foreign body.

There is a medical material made of freeze-dried dura mater encephali, a connective tissue membrane, collected from human cadaver specimens. The freeze-dried dura mater encephali is the only homologous medical material that has been approved as wound filler for replacement. However, in recent years, serious side effects and concerns such as that of prion, a pathogen of transmissible Creutzfeldt-Jakob syndrome, have been pointed out, as this medical material contains cellular substances such as epithelial and fibroblast layers of connective tissue membrane.

Moreover, there are also medical materials made of natural or synthetic macromolecular or polymeric materials, and medical materials for implants in which the raw material is equine or bovine pericardium that is completely modified chemically with glutaraldehyde, having nearly the same characteristics as synthetic macromolecular materials which are insoluble, non-degradable and non-absorbable in the body. Such medical materials, when implanted in the body, become encapsulated with endothelium. Such encapsulation is a physiologic phenomenon of self defense in response to the foreign body. The capsule thickens and becomes hypertrophic with time, remaining in the body permanently. This is an abnormal phenomenon for the body and causes naturally incoherence and imbalance in existence and growth between the implant site and surrounding normal tissues, possibly causing untoward results.

Since January, Showa 58 (1983), the present inventors and/or their collaborators have conducted studies on the technique and applied for various patents. Such techniques are described below.

Japanese Patent No. 1641621 is concerned with a medical material of membranous or tubular configuration for prosthesis for bladder, urethra and ureter. The medical material is made of composite materials of natural or synthetic macromolecular fiber and human amnion. This medical material failed to achieve complete antigenic or allergic biocompatibility and had the drawback of being non-degradable and insoluble, remaining in the body as a foreign body.

Unexamined Japanese Patent Publication Hei No. 7-116242 (i.e., 116242/95) is concerned with a medical material comprising two collagenous membranes and a mesh-like intermediate material inbetween, glued together with an adhesive. Namely this medical material is a composite substance comprising collagen-like membranes and an intermediate mesh-like material of synthetic fiber. The "collagen-like membrane" described here includes silicon membrane, gelatin membrane, other natural macromolecular gel membrane and synthetic macromolecular gel membrane. Therefore that term is not a scientifically well-accepted term but is a very indefinite term. In addition, the membrane retains the foreign-body reaction characteristic of synthetic fiber.

Unexamined Japanese Patent Publication Hei No. 7-213597 (i.e., 213597/95), published Aug. 13, 1995, discloses a purified collagen-like substance. The "purified collagen-like substance" used in Example 1, described in the specification was stated clearly as "a compact layer of human amnion". The patent is concerned with a twisted thread made of the compact layer of the human amnion, with medical materials made of the twisted thread and with manufacturing methods of the thread and the medical materials. The technique disclosed in the patent had a drawback of lacking physical strength, as physical strength depended on cross-linking density solely between collagen molecules in the substrate material.

As described above, existing medical materials are found to cause some concerns to the body and/or to have insufficient physical conditions required in surgical maneuvers. In the present invention, it is attempted to provide a safe, effective and useful medical material, i.e., an ultimately ideal medical material. The ultimately ideal medical material for treatment used in the surgical field is one that simultaneously satisfies safety, effectiveness and usefulness listed below.

(1) Safety: devices for implant that are used for treating bones or tissues and remain in contact with the body for a long period of time (30 days or longer) must be proven safe in tests for cytotoxicity, sensitization, subacute toxicity, implantation and others according to methods established in the International Organization for Standardization (ISO). Furthermore, laws require that each device must be proven for prescribed safety based on safety criteria in wide-ranged chemical, physical and biological tests according to the provisions. The ISO guideline of safety for surface-contacting devices has lists of tests, methods and evaluation criteria that are classified by contact sites; skin, mucous membrane and damaged surface, and require to prove the safety. In addition, devices must meet safety criteria determined by the laws. Medical devices originating from biological tissues must be proven completely safe, in addition to all of the above, from medical risk of pathogens including virus and bacteria which are the infectious pathogens of hepatitis (types A, B and C), HIV or venereal disease and prion which is a transmissible pathogen of Creutzfeldt-Jakob syndrome.

(2) Effectiveness of medical devices used as wound prosthesis or dressing: unless physiological function in addition to physical and mechanical function is satisfactory, the medical material is not recognized as being ultimately ideal. The ultimately ideal conditions for the physical and mechanical functions are that the medical materials applied to defective lesions can be used satisfactorily in any technique; adhesion with adhesives, manual and mechanical sutures, and the material can adhere and fix the normal tissues and organs after defective lesions are resected and removed. The material also must have properties that are consistent with physical and mechanical functions of normal tissues and organs.

The ultimately ideal conditions of physiological function described above must simultaneously satisfy the conditions listed below.

(1) Medical material should be a homologous material.

(2) Surgical sites of the body are replaced with normal tissues as medical materials decompose and are absorbed under ideal conditions as time passes.

(3) Oozing and leakage of blood and body fluid and leakage of gas are inhibited at surgical sites.

(4) Drainage is unnecessary.

(5) Materials have ideal qualities and physical and mechanical strength.

(6) Surgical technique is made easier, surgical time is shortened and early cure is made possible.

The scientific principles explaining the condition (1) and (2) described above can be summarized as following. The science of the connective tissue has established theory of principles regarding "cell proliferation and extracellular matrix" and "damage healing and extracellular matrix". It is a scientific principle regarding physiological mechanism of the body in which damaged sites self-repair as tissue is formed by cell proliferation. The connective tissue is composed with laminated layers of, in order, epithelium layer, basement membrane layer, compact layer and fibroblast layer. The mechanism of formation of connective tissue is thought to be that specific cells for the connective tissue are taken into the compact layer. As the taken cell proliferates, other layers are formed in succession, making connective tissue. Essential conditions for cell proliferation are said to be the ideal matrix, formed by collagen fiber that is made up with various collagens which constitute the compact layer, and cell growth factor substances. According to this scientific principle, a medical material that satisfies the ultimately ideal condition of physiological function is a homologous medical material that preserves the matrix of the compact layer which comprises various types of human collagen which constitutes human connective tissue.

(3) Usefulness: medical material should be developed for patients and for advancement and improvement of medical welfare. That is to say that the ultimately ideal medical material is one with usefulness that satisfies conditions of early healing of diseases, early discharge of patients, shortened surgical time (usefulness to surgeons), stable quantity of supply (fairness of welfare), long-term stability of quality standard and reasonable cost.

In light of the ideal conditions described above that the ultimately ideal medical material must possess, medical materials made with conventional technique have those fundamental and essential defects listed below.

(1) Medical materials of natural or synthetic macromolecular materials or medical materials, such as implants made of raw material of equine or swine pericardium that is completely modified chemically with glutaraldehyde to be insolvable, non-degradable and non-absorbable characteristics nearly similar to that of synthetic macromolecules, are capsulated with endothelium. The capsulation is due to physiological phenomenon of self-defence response to a foreign body. The capsule thickens and becomes hypertrophic with time, remaining in the body permanently. Such an abnormal phenomenon for the body causes naturally incoherence and imbalance in existence and growth between the implant site and surrounding normal tissues. The materials do not eliminate the risk of developing inconvenient situation.

(2) Freeze-dried dura mater encephali, that has been approved and marketed as a homologous wound prosthesis for replacement is made of raw material of dura mater encephali collected from human cadaver, does not eliminate medical risk caused by transmissible pathogen prion and unstable quantity of supply as well as high cost.

(3) Medical materials marketed currently as wound dressings include swine skin, plastic film, non-woven fabric of alginic acid fiber and other various products. All these products leave keloid or scar at the treated sites and require renewal more than once during the healing period. They are mere substitutes until the ultimately ideal wound dressing appears.

(4) There is medical material made of type I collagen that is extracted and purified from corium of bovine or swine skin, and then telopeptide is removed. Medical materials made of such collagen also are not free from following defects; industrial means and technique are unable to eliminate antigenicity completely, physiological function of tissue regeneration is lacking, as the extracellular matrix which is considered to be the essential condition for regeneration of connective tissue is not formed, the material is a synthetic macromolecular compound which is completely modified chemically with glutaraldehyde and the like, and is physiologically analogous to plastic and the risks caused by slow virus such as AIDS virus and transmissible pathogens prion. The material is also a mere substitute.

(5) As a medical material that possesses degradability and absorbability in the body, suture made of animal intestine exists. The suture has the problems of persistent pathogens as with the collagen described above and of residual keloid and scar formation. Thread of polyglycolic acid (PGA) is marketed as degradable and absorbable suture, PGA mesh and non-woven fabric. The PGA thread, however, has persistent problems of carbohydrate-caused allergy and irritation.

It is attempted in the present invention to develop a medical material that will solve all problems caused by various factors remaining in existing techniques and satisfy the ultimate ideal conditions.

SUMMARY OF THE INVENTION

The inventions studied attempting to develop the ultimate medical material that can solve the above problems and complete the invention.

A first aspect of the present invention provides a medical or surgical material. The medical or surgical material is of membranous substance which is only an acellular layer of a connective tissue of a living body and consists essentially of a compact layer of the connecting tissue. The medical or surgical material is produced by impregnating the membranous material with collagen or gelatin, and physically or chemically forming cross-linkings between structuring protein molecules. In one embodiment, the medical or surgical material has a membrane configuration having sufficient physical strengths to make manual and mechanical suture in surgery possible. In another embodiment, the medical or surgical material has a thread or string configuration and is made of the membranous material. In still another embodiment the medical material has a tube or hose configuration made of the thread or string.

A second aspect of the present invention provides manufacturing methods of the medical or surgical material.

DESCRIPTION OF PREFERRED EMBODIMENTS

In the field of physiology, connective tissue is classified by function and divided into four layers of epithelium, basement membrane, compact and fibroblast to study the structural form. In the field of optical microscopic science, it is classified visually and divided into three layers of epithelium, basement membrane and fibroblast. That is to say, the basement membrane layer and the compact layer which are considered as two separate layers in physiology are collectively called as the basement membrane layer in optical microscopical science. The epithelial and fibroblast layers are cellular in nature and the basement membrane and compact layers are acellular in nature. The thickness of the basement membrane layer is extremely small and is expressed in nanometers, while that of the compact layer can be expressed in micrometers.

The connective tissue useful according to the invention includes biogenic membranes such as dura mater encephali, pericardium, pleura, pelviperitoneum, diaphragm, peritoneum, fascia, mesenterium, skin and tympanic membrane; external walls of biogenic organs such as vascular wall, oesophageal wall, tracheal wall, urethral wall, ureteral wall and cardiac wall. In addition, fetal membrane and amnion which constitutes the former, and chorion etc. may also be included. Human amnion is approximately 12,000 nanometer in thickness and comprises, as the boundary layer, the basement membrane layer (50–80 nanometer thick) and the compact layer (8,000–10,000 nanometer thick), and the epithelial layer and fibroblast layer at the each outer side. The compact layer in the instant specification is a combination of the compact layer and basement membrane layer in optical microscopic science and substantially the compact layer in the field of physiology.

The membranous substance which consists essentially of a compact layer that is only an acellular layer of a biogenic connective tissue used in conducting the invention is a medical material that satisfies the ultimately ideal conditions concerning physiological function and biocompatibility thereof. However, physical nature of the material resembles that of wafer sheet, in particular, it contracts extremely when it is humid and as it is extremely weak. Therefore it is not possible to be sutured and is difficult to handle in surgery in which a medical material gets wet with a body fluid.

Such a membranous substance consisting essentially of a compact layer of a biogenic connective tissue may be obtained by removing the epithelium and fibroblast layers from the connective tissue. For example, human fetal membrane which is normally disposed of as waste, may be separated into amnion and chorion. The amnion is treated with thiolprotease such as ficin and then with ultrasonic washing to obtain the compact layer. Such a process is described for example in above-mentioned Unexamined Japanese Patent Publication No. 7-213597.

In the compact layer of human amnion and human chorion which are human connective tissue, collagen of types I, III and V forms a filamentous matrix. In addition, collaborators of the inventors discovered the existence of type XVI collagen and reported it in J. Biochem., 112, 856–863 (1992). In other words, the compact layer is composed principally of collagen. Therefore, the compact layer possesses chemical characteristics that are specific to collagen.

Cross-linkings between collagen molecules can be formed by physical energy such as heating or irradiation with ultraviolet rays, electron beam and radiation. This is called as physical modification of collagen. Cross-linkings between collagen molecules can also be formed by chemicals such as formaldehyde and glutaraldehyde. This is called as chemical modification of collagen. In the cross-linking reaction between collagen molecules by physical or chemical modification of collagen, the cross-linking reaction is believed to occur between animo groups which are side chain groups of collagen molecules.

The cross-linkings between collagen molecules can increase physical strength of collagen composition. However, even when cross-linkings are formed between all amino groups which are the functional groups in collagen molecules of the compact layer made essentially of collagen, the compact layer that is so modified physically or chemically is not fiber-enforced and does demonstrate physical properties appropriate for suture and other maneuvers in surgery. This is because the density of cross-linking is insufficient due to a small number of amino groups which are the functional groups in collagen molecules constituting the compact layer.

Gelatin, although of a physical nature different from that of collagen, is a protein having the same chemical composition as that of collagen. Therefore, gelatin, like collagen, has amino groups, which are functional groups, and can be cross-linked by physical or chemical modification between protein molecules.

According to the present invention, a medical material with physical nature and strength that satisfies conditions of surgical maneuvers may be obtained without using chemical substances that have different compositions from that of the compact layer.

Collagen used in the present invention is animal-originated, extracted and purified collagen from which telopeptide is removed. The collagen is preferably human-originated, extracted and purified collagen, and more preferably human fetus-originated collagen.

Gelatin used in the present invention is purified gelatin for injection indicated in The Pharmacopoeia of Japan (JP), and preferably a gelatin with similar quality to JP purified gelatin for injection that is manufactured from human-originated collagen.

The formation of the cross-linkings may be carried out by generally known methods. A preferred method involves simply heating the membranous material impregnated with collagen or gelatin at a temperature at which the cross-linkings are formed, for example, at 80° to 130° C, more preferably at 100° to 110° C.

According to the present invention, physical strength of the membranous material can be increased considerably by impregnating the compact layer membrane with collagen or gelatin, followed by simultaneously forming cross-linkings between collagen molecules in the compact layer and between protein molecules in impregnated collagen or gelatin. Thus, the density of cross-linking between protein molecules in the membranous material is increased extremely.

As a result, it was proven that physical strength of the membranous material according to the invention was markedly increased compared to membranous materials in which the compact layer only was cross-linked. As demonstrated in Example 1, an example of results of experiments is shown in Table 1.

TABLE 1

|  | Thickness (μm) | Tensile strength (Kgf/cm$^2$) | Elongation (%) |
| --- | --- | --- | --- |
| (1) Untreated compact layer membrane | 4.5 | 470 | 13.7 |

TABLE 1-continued

|  | Thickness (μm) | Tensile strength (Kgf/cm²) | Elongation (%) |
|---|---|---|---|
| (2) Cross-linked compact layer membrane | 4.1 | 300 | 8.8 |
| (3) Cross-linked and gelatin impregnated compact layer membrane | 14.0 | 631 | 5.0 |

The medical material according to the present invention manufactured by the above process not only makes manual and mechanical sutures in surgery possible but also displays the characteristic that it maintains configuration even when wet with blood or body fluid. Moreover, this material is easy to handle. Therefore, medical materials of membrane configuration are useful as a wound filler or wound prostheses that are implanted and as wound, burn and scald dressings and skin graft for donor of grafting for external use. Medical materials of thread configuration are used for suture and medical materials of hose or tube configuration can be employed as artificial blood vessels, ureter, urethra, trachea and oesophagus.

For better understanding of the invention the following examples may be helpful. However, it should be borne in mind that the present invention is not limited to these examples.

EXAMPLE 1

Two grams of JP purified gelatin for injection were weighed and collected, and then were dissolved in 100 ml JP purified water at 60° C. The solution was left to cool to room temperature. This is called as a gelatin aqueous solution hereafter. The gelatin aqueous solution was poured in a dish of 30 cm×15 cm×2 cm (depth) in size until surface reaches 1 cm deep and was left at room temperature. By dipping and rolling a ceramic roller of 3 cm in diameter×10 cm long in the gelatin aqueous solution in the dish described above, the gelatin aqueous solution became attached to the surface of the roller.

On a polyethylene plate of 5 cm thick×30 cm wide×50 cm long, a compact layer membrane was left to stand after being dilated. The gelatin aqueous solution was rubbed into the compact layer membrane by rolling the roller to which gelatin aqueous solution was attached. By repeating the procedure, the compact layer membrane became impregnated with gelatin aqueous solution until saturated with the gelatin aqueous solution. The compact layer membrane impregnated with the gelatin aqueous solution was heated and dried at 105° C. for 24 hours for cross-linking under reduced pressure and suction.

In order to eliminate from the cross-linked membranous material, the risk of antigenicity caused by residual amino groups that had not reacted, the membrane was subjected to succinylation reaction as follows. A mixed solution comprising 500 ml of 0.02M borate buffer solution (pH 9.0) and 100 ml of 5% succinic anhydride in acetone is termed the succinylation-adjusted solution. After being left for four hours for succinylation in a vessel filled with the succinylation-adjusted solution, the cross-linked membranous material was washed with JP purified water to remove the succinylation-adjusted solution, and then was dried with 30° C. dried aseptic warm air for approximately 12 hours in a vacuum oven. The product, the subject matter of the invention, was acquired. Physical characteristics of the product are shown in Table 1 mentioned above.

The medical material with cross-linked structure according to the present invention was thus produced in the process described above. When the acquired product was tested in ninhydrin method, no color development was observed. Therefore, it was proven that the cross-linking reaction was complete between collagen molecules of which the compact layer membrane is made and between gelatin molecules that were impregnated, and that no unreacted amino group remained.

EXAMPLE 2

In this example, collagen was employed. Using collagen in 1 ml of 3% solution of Koken Atherocollagen Implant (a trade mark of Koken Co., Ltd.), or referring to a very ordinary preparation method described in the Chapter 1 "Preparation of Collagen" in the "Experimental Methods of Collagen" published by Kodanshe Co., Ltd., 0.004% human collagen neutral buffer solution was prepared from human amnion or chorion. This is called as a collagen solution hereafter. By the same procedure as in Example 1, except using the above collagen solution in place of the gelatin solution, the medical material, the object of the invention, was acquired.

Tests of absorption and tissue reaction were conducted with the physically modified membrane of the medical material of the invention obtained in Example 1, in muscles at back region of rabbits. Results of the tests are shown in Tables 2 and 3.

TABLE 2

Absorption of physically modified membrane of the compact layer membrane that originated from human amnion in muscles at back region of rabbits

| | Duration | | |
|---|---|---|---|
| | 2 Weeks | 4 Weeks | 6 Weeks |
| Physically modified compact layer membrane | Embrittlement of membrane 3/5 Membrane broken 2/5 | Membrane absorbed 3/4 Partial membrane persisted 1/4 | Membrane absorbed 2/3 Partial membrane persisted 1/3 |
| | 8 Weeks | 12 Weeks | 16 Weeks |
| Physically modified compact layer membrane | Membrane absorbed 3/3 | Membrane absorbed 3/3 | Membrane absorbed 3/3 |

TABLE 3

Tissue reaction of physically modified membrane of the compact layer membrane originated from human amnion in muscles at back region of rabbits

| | Duration | | |
|---|---|---|---|
| | 2 Weeks | 4 Weeks | 6 Weeks |
| Physically modified compact layer membrane | Infiltration of inflammatory cells mild 2/5 none 3/5 | Infiltration of inflammatory cells mild 4/4 | Infiltration of inflammatory cells mild 3/3 |
| | 8 Weeks | 12 Weeks | 16 Weeks |

TABLE 3-continued

Tissue reaction of physically modified membrane of the compact layer membrane originated from human amnion in muscles at back region of rabbits

| | Duration | | |
|---|---|---|---|
| Physically modified compact layer membrane | Infiltration of inflammatory cells mile 1/3 none 2/3 | Adipose tissue partial fibrous tissue 3/3 | Adipose tissue partial fibrous tissue 3/3 |

Tables 2 and 3 show the results of experiments using animals according to clinical tests criteria and manufacture approval criteria relating to the product of the present invention. The product according to the present invention was implanted in muscles at back region of male white rabbits. Tissue samples of the implanted region were taken every two weeks after the implantation and the samples were absorbed and evaluated according to standard methods of experimental pathology.

The results in Table 2 indicate that the implanted test product was being decomposed and absorbed in the living body for six weeks after the implantation and demonstrate that the decomposition and absorption of the implanted test product was complete in eight weeks from the implantation. In other words, these results show the progress in which the implanted test product becomes homogenized with the living body while the test product is decomposed and absorbed in the living body and in which the muscle tissues around the implanted product in the rabbit back region regenerate themselves and replace the implanted product, as well as the completed conditions of the progress. The results demonstrate the usefulness of the test product as a medical material.

The results in Table 3 indicate that no generation of abnormal cells such as deformed or cancerous cells was observed with respect to the tissue samples periodically taken and prepared as shown in Table 2. These results demonstrate the safety of the test product.

We claim:

1. A medical material of a membrane configuration made of a membranous material which consists essentially of a compact layer that is only an acellular layer of a biogenic connective tissue and which is produced by impregnating with collagen or gelatin and then forming physical or chemical cross-linkings between protein molecules of the compact layer, the medical material having sufficient physical strength to be useful for manual or mechanical suture in surgery.

2. A medical material of a thread or string configuration made from a membranous material which consists essentially of a compact layer that is only an acellular layer of a biogenic connective tissue and which is impregnated with collagen or gelatin, wherein physical or chemical cross-linkings are formed between protein molecules of the compact layer so that the thread or string configuration is stably maintained and has sufficient physical strength to be useful in surgery.

3. A medical material of a tube or hose configuration made from a thread or string made in turn from a membranous material which consists essentially of a compact layer that is only an acellular layer of a biogenic connective tissue and which is impregnated with collagen or gelatin, wherein physical or chemical cross-linkings are formed between protein molecules of the compact layer so that the tube or hose configuration is stably maintained and has sufficient strength to be useful in surgery.

4. A medical material according to claim 1, wherein the biogenic connective tissue is human amnion.

5. A medical material according to claim 4, wherein the collagen is human-originated, extracted and purified collagen from which telopeptide has been removed; and the gelatin is purified gelatin having a quality for injection and being manufactured from human-originated collagen.

6. A medical material according to claim 5, wherein the physical cross-linkings are formed by heating the compact layer impregnated with collagen or gelatin.

7. A medical material according to claim 5, which has been treated with succinic anhydride for eliminating antigenicity caused by possibly remaining unreacted amino groups after the formation of the cross-linkings.

8. A method for manufacturing a medical material having a membrane configuration, a thread or string configuration or a tube or hose configuration, which comprises, providing a membranous material which consists essentially of a compact layer that is only an acellular layer of a biogenic connective tissue;

impregnating the membranous material with collagen or gelatin;

forming physical or chemical cross-linkings between protein molecules of the compact layer to such an extent that the resulting material has sufficient physical strength to be useful for manual or mechanical suture in surgery;

where required, forming a thread or string from the resulting material; and where further required, forming a tube or hose from the thread or string.

9. A method according to claim 8, wherein the biogenic connective tissue is human amnion; the collagen is human-originated, extracted and purified collagen from which telopeptide has been removed; and the gelatin is purified gelatin having a quality for injection and being manufactured from human-originated collagen.

10. A method according to claim 9, wherein the physical cross-linkings are formed by heating the compact layer impregnated with collagen or gelatin.

* * * * *

UNITED STATES PATENT AND TRADEMARK OFFICE
CERTIFICATE OF CORRECTION

PATENT NO. : 5,618,312
DATED : April 8, 1997
INVENTOR(S) : Tooru Yui, et al.

It is certified that error appears in the above-identified patent and that said Letters Patent is hereby corrected as shown below:

Column 2, line 5, "silicon" should read --silicone--.

Column 4, line 47, "connecting" should read --connective--.

Column 6, line 2, "animo groups" should read --amino groups--;
        line 10, "does demonstrate" should read
    --does not demonstrate--.

Signed and Sealed this

Twenty-fourth Day of February, 1998

*Attest:*

BRUCE LEHMAN

*Attesting Officer*     *Commissioner of Patents and Trademarks*